US012705711B2

(12) United States Patent
Sakaguchi et al.

(10) Patent No.: US 12,705,711 B2
(45) Date of Patent: Aug. 11, 2026

(54) PROGRAM, IMAGE PROCESSING METHOD, AND IMAGE PROCESSING DEVICE

(71) Applicant: TERUMO KABUSHIKI KAISHA, Tokyo (JP)

(72) Inventors: Yuki Sakaguchi, Fujisawa (JP); Kohtaroh Kusu, Ebina (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 332 days.

(21) Appl. No.: 18/468,205

(22) Filed: Sep. 15, 2023

(65) Prior Publication Data

US 2024/0005459 A1 Jan. 4, 2024

Related U.S. Application Data

(63) Continuation of application No. PCT/JP2022/010187, filed on Mar. 9, 2022.

(30) Foreign Application Priority Data

Mar. 26, 2021 (JP) ................................ 2021-053667

(51) Int. Cl.
*G06T 5/77* (2024.01)
*A61B 6/00* (2024.01)
(Continued)

(52) U.S. Cl.
CPC .............. *G06T 5/77* (2024.01); *G06V 10/752* (2022.01); *A61B 6/487* (2013.01); *A61B 8/0891* (2013.01);
(Continued)

(58) Field of Classification Search
CPC ............... G06V 10/752; G06V 10/764; G06V 2201/031; G06V 2201/03; G06V 10/25;
(Continued)

(56) References Cited

U.S. PATENT DOCUMENTS 6,233,476 B1 5/2001 Strommer et al.
11,122,981 B2 * 9/2021 Olender .............. A61B 5/0035
(Continued)

FOREIGN PATENT DOCUMENTS

JP 2003520062 A 7/2003
JP 2004533863 A 11/2004
(Continued)

OTHER PUBLICATIONS

English Translations of the International Search Report (Form PCT/ISA/210) and the Written Opinion of the International Searching Authority (Form PCT/ISA/237) issued May 17, 2022, by the Japan Patent Office in corresponding International Application No. PCT/JP2022/010187. (7 pages).

(Continued)

*Primary Examiner* — Chan S Park
*Assistant Examiner* — Chandhana Pedapati
(74) *Attorney, Agent, or Firm* — Buchanan Ingersoll & Rooney PC

(57) ABSTRACT

A non-transitory computer-readable medium storing a computer program executed by a computer, a method, and an image processing device are disclosed that are capable of compensating a missing region in a tomographic image in a state in which a part of a lumen organ is missing. In accordance with the program, a computer acquires a plurality of tomographic images of a cross section of the lumen organ captured at a plurality of places using a catheter. In addition, the computer extracts, from the plurality of tomographic images, a tomographic image in which the part of the lumen organ is missing. Then, the computer compensates a missing region of the lumen organ for the extracted tomographic image.

20 Claims, 11 Drawing Sheets

(51) Int. Cl.
*A61B 8/08* (2006.01)
*A61B 8/12* (2006.01)
*G06V 10/75* (2022.01)

(52) U.S. Cl.
CPC ....... *A61B 8/12* (2013.01); *G06T 2207/10072* (2013.01); *G06T 2207/20081* (2013.01); *G06T 2207/30101* (2013.01); *G06V 2201/031* (2022.01)

(58) Field of Classification Search
CPC ......... A61B 8/0891; A61B 8/12; A61B 6/487; A61B 8/5261; A61B 8/14; G06T 2207/10072; G06T 2207/20081; G06T 7/62; G06T 2207/30101; G06T 7/0012; G06T 2207/10101; G06T 2207/10121; G06T 2207/10132; G06T 5/77; G06T 7/12; G06T 2207/10016; G06T 2207/20084; G06T 5/50
See application file for complete search history.

(56) References Cited

U.S. PATENT DOCUMENTS

2002/0049375 A1 4/2002 Strommer et al.
2006/0079772 A1 4/2006 Ichikawa et al.
2011/0071404 A1* 3/2011 Schmitt ............. A61B 5/02007 382/128
2011/0251454 A1* 10/2011 Robb ..................... A61B 5/064 600/103
2016/0022208 A1 1/2016 Gopinath
2019/0021694 A1 1/2019 Sakaguchi
2019/0336033 A1 11/2019 Takeshima
2020/0226422 A1 7/2020 Li et al.
2021/0137491 A1 5/2021 Sakamoto et al.

FOREIGN PATENT DOCUMENTS

JP 2005000638 A 1/2005
JP 2017527418 A 9/2017
JP 2018075080 A 5/2018
JP 2020175009 A 10/2020
WO WO-2014055923 A2 * 4/2014 ......... A61B 5/02007
WO 2017164071 A1 9/2017
WO 2019102846 A1 5/2019
WO 2019189519 A1 10/2019

OTHER PUBLICATIONS

International Search Report (PCT/ISA/210) with translation and Written Opinion (PCT/ISA/237) mailed on May 17, 2022, by the Japan Patent Office as the International Searching Authority for International Application No. PCT/JP2022/010187. (11 pages).

* cited by examiner

IVUS IMAGE

FIRST LEARNING MODEL

M2

SECOND LEARNING MODEL

PROGRAM, IMAGE PROCESSING METHOD, AND IMAGE PROCESSING DEVICE

CROSS-REFERENCES TO RELATED APPLICATIONS

This application is a continuation of International Application No. PCT/JP2022/010187 filed on Mar. 9, 2022, which claims priority to Japanese Application No. 2021-053667 filed on Mar. 26, 2021, the entire content of both of which is incorporated herein by reference.

TECHNOLOGICAL FIELD

The present disclosure generally relates to a program, an image processing method, and an image processing device.

BACKGROUND DISCUSSION

A catheter system for capturing a tomographic image by inserting an image diagnosis catheter into a lumen organ such as a blood vessel is used (see International Patent Publication No. WO2017/164071).

When an image diagnosis catheter is used, a tomographic image is captured with a circular region, in which a center of a catheter is an imaging center, as an imaging range. The image diagnosis catheter is not limited to being located at a center of the lumen organ, and an image is captured at a position in which the lumen organ is biased with respect to the imaging range when the catheter is located at a vicinity of the lumen wall. In particular, in a large blood vessel such as a coronary artery, a cross section of the blood vessel does not fall within an imaging range, and a tomographic image may be obtained in a state in which a part of the blood vessel is missing. In this way, in the tomographic image in the state in which the part of the lumen organ is missing, it is not possible to appropriately determine a state of the lumen organ, and interpretation of the tomographic image can be complicated. A size of a lumen of the lumen organ and a thickness of the lumen wall are calculated from the tomographic image, but there is a problem that these pieces of information cannot be accurately calculated in the tomographic image in which the part of the lumen organ is missing.

SUMMARY

A non-transitory computer-readable medium storing a computer program that is capable of compensating a missing region in a tomographic image in a state in which a part of a lumen organ is missing.

A non-transitory computer-readable medium storing a computer program according to an aspect that causes a computer to execute a process comprising: acquiring a plurality of tomographic images of a cross section of a lumen organ captured at a plurality of places using a catheter; extracting, from the plurality of tomographic images, a tomographic image in which a part of the lumen organ is missing; and compensating a missing region of the lumen organ for the extracted tomographic image.

An image processing method of executing processes by a computer according another aspect, the image processing method comprising: acquiring a plurality of tomographic images of a cross section of a lumen organ captured at a plurality of places using a catheter; extracting, from the plurality of tomographic images, a tomographic image in which a part of the lumen organ is missing; and compensating a missing region of the lumen organ for the extracted tomographic image.

An image processing device according to an aspect comprising: a processor configured to: acquire a plurality of tomographic images of a cross section of a lumen organ captured at a plurality of places using a catheter; extract, from the plurality of tomographic images, a tomographic image in which a part of the lumen organ is missing; and compensate a missing region of the lumen organ for the extracted tomographic image.

In one aspect, a missing region in a tomographic image in a state in which a part of a lumen organ is missing can be compensated (or complemented).

BRIEF DESCRIPTION OF THE DRAWINGS

FIG. 13 is a schematic diagram showing a modification of the second learning model.

DETAILED DESCRIPTION

Set forth below with reference to the accompanying drawings is a detailed description of embodiments of a non-transitory computer-readable medium storing a computer program executed by a computer, an image processing method, and an image processing device. In the following embodiments, cardiac catheter treatment, that is, intravascular treatment, will be described as an example, but a lumen organ targeted for catheter treatment is not limited to a blood vessel, and may be other lumen organs such as a bile duct, a pancreatic duct, a bronchus, and an intestine.

Embodiment 1

Figure 1:
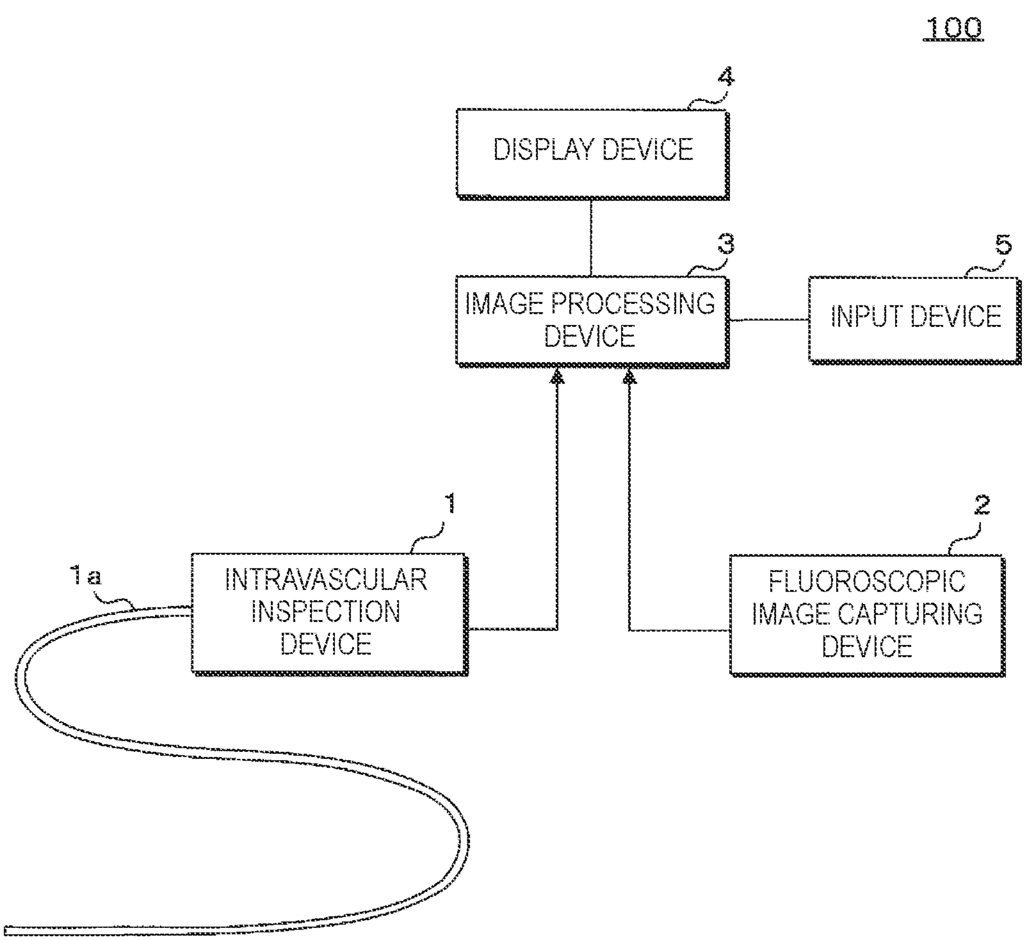
FIG. 1 is a schematic diagram showing a configuration example of an image diagnosis apparatus.

FIG. 1 is a schematic diagram showing a configuration example of an image diagnosis apparatus 100. The image diagnosis apparatus 100 according to the present embodiment can include an intravascular inspection device 1, a fluoroscopic image capturing device 2, an image processing device 3, a display device 4, and an input device 5. The intravascular inspection device 1 is a device for imaging an intravascular tomographic image of a patient, and can be, for example, an intravascular ultrasound (IVUS) device that performs an ultrasound inspection using a catheter 1*a*. The catheter 1*a* is a medical instrument to be inserted into a blood vessel of the patient, and can include an ultrasound transmitter and receiver that transmits an ultrasonic wave and receives a reflected wave from the blood vessel. The intravascular inspection device 1 generates an ultrasound tomographic image (IVUS image) obtained by imaging a cross section of the blood vessel based on a signal of the reflected wave received by the catheter 1*a*, and displays the ultrasound tomographic image on the display device 4 by the image processing device 3. In the present embodiment, the intravascular inspection device 1 generates the ultrasound tomographic image, but an optical coherence tomography image (OCT image) captured by an optical coherence tomography (OCT) diagnosis method may be generated. In this case, the catheter 1*a* includes an optical transmitter and receiver that transmits near infrared light and receives reflected light from the blood vessel.

The fluoroscopic image capturing device 2 is a device for capturing a fluoroscopic image of an inside of a body of the patient, and can be, for example, an angiography device for imaging the blood vessel using an X-ray from outside of the body of the patient to obtain an angiogram which is a fluoroscopic image of the blood vessel. The fluoroscopic image capturing device 2 can include an X-ray source and an X-ray sensor, and obtains an X-ray fluoroscopic image of the patient by the X-ray sensor receiving the X-ray emitted from the X-ray source. A marker made of a radiopaque material that does not transmit the X-ray can be attached to a distal end of the catheter 1*a*, and a position of the catheter 1*a* can be visualized in the fluoroscopic image. The fluoroscopic image captured by the fluoroscopic image capturing device 2 is displayed on the display device 4 by the image processing device 3, and the fluoroscopic image in which the position of the catheter 1*a* (marker) is visualized is presented to an operator together with the intravascular tomographic image. In the present embodiment, the image diagnosis apparatus 100 includes the fluoroscopic image capturing device 2 which captures a two-dimensional angiogram, and is not particularly limited as long as the image diagnosis apparatus is an apparatus that images the lumen organ of the patient and the catheter 1*a* from a plurality of directions outside the body.

The display device 4 and the input device 5 are connected to the image processing device 3. The display device 4 can be, for example, a liquid crystal display or an organic EL display, and displays a medical image such as the IVUS image captured by the intravascular inspection device 1 and the angiogram captured by the fluoroscopic image capturing device 2. The input device 5 can be, for example, a keyboard, a mouse, a track ball, or a microphone, and receives various operations by the operator. The display device 4 and the input device 5 may be integrally stacked (or integrated) to form a touch panel. The input device 5 and the image processing device 3 may be integrally formed. Further, the input device 5 may be a sensor that receives gesture input, eye-gaze input, or the like.

Figure 2A:
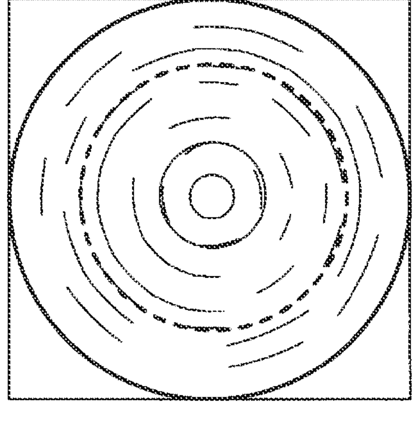
FIG. 2A is a schematic diagram showing an example of an IVUS image captured by an intravascular inspection device.
Figure 2B:
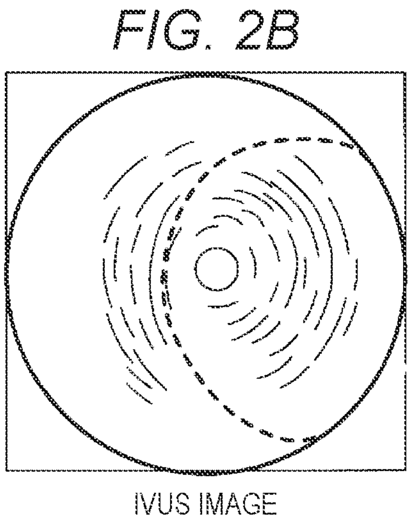
FIG. 2B is a schematic diagram showing an example of the IVUS image captured by the intravascular inspection device.

FIGS. 2A and 2B are schematic diagrams showing examples of the IVUS image captured by the intravascular inspection device 1. In the intravascular inspection device 1, the IVUS image (tomographic image) is captured with a circular region, in which a center of the catheter 1*a* is an imaging center, as an imaging range, regions surrounded by circles indicated by solid lines in FIGS. 2A and 2B are imaging ranges, and a contour line (contour) of the IVUS image is indicated by a circle. In general, the IVUS image is presented to the operator as square images as shown in FIGS. 2A and 2B, and the square images are generated and presented by adding, for example, black pixels to a region outside the imaging range, that is, a region outside the circle. Therefore, in the present embodiment, the contour line of the IVUS image (tomographic image) means the circles in FIGS. 2A and 2B.

FIG. 2A is an example of the IVUS image captured when the catheter 1*a* is located at a center of the intravascular lumen, and FIG. 2B is an example of the IVUS image captured when the catheter 1*a* is located at a vicinity of a vessel wall (lumen wall). Broken lines in FIGS. 2A and 2B schematically indicate contour lines of the blood vessel (outer contour lines of the vessel wall). As shown in FIG. 2A, when the catheter 1*a* is located at the center of the intravascular lumen, the entire blood vessel falls within the imaging range, and a tomographic image (IVUS image) in which the entire blood vessel is imaged is obtained. Meanwhile, when the catheter 1*a* is located at a position biased (i.e., not centered) to the vessel wall, a part of the blood vessel does not fall within the imaging range, and as shown in FIG. 2B, a tomographic image (IVUS image) in a state in which a part of the blood vessel is missing is obtained. The image processing device 3 according to the present embodiment performs a process of compensating a missing region for an IVUS image in the state in which the part of the blood vessel is missing as shown in FIG. 2B. Hereinafter, the IVUS image in the state in which the part of the blood vessel is missing is referred to as an IVUS image in which the blood vessel is framed out, and the IVUS image in a state in which the blood vessel is not missing is referred to as an IVUS image in which the blood vessel is not framed out.

Figure 3:
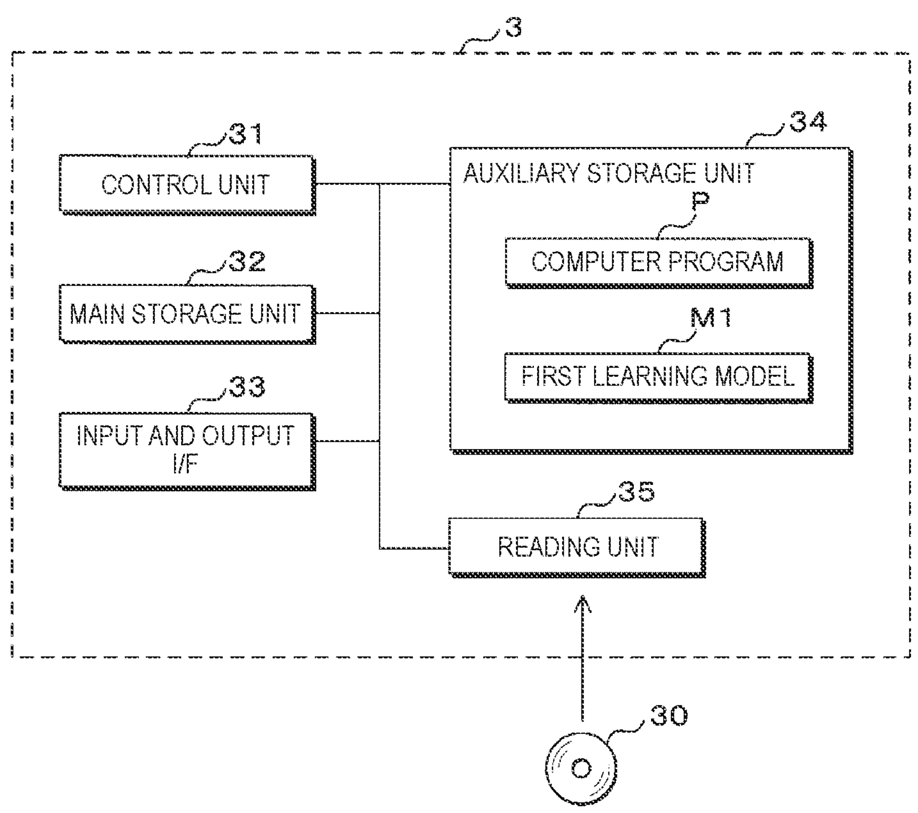
FIG. 3 is a block diagram showing a configuration example of an image processing device.

FIG. 3 is a block diagram showing a configuration example of the image processing device 3. The image processing device 3 is a computer and can include a control unit 31, a main storage unit 32, an input and output I/F 33, an auxiliary storage unit 34, and a reading unit 35. The control unit 31 can include one or a plurality of arithmetic processing units such as a central processing unit (CPU), a micro-processing unit (MPU), a graphics processing unit (GPU), general-purpose computing on graphics processing units (GPGPU), and a tensor processing unit (TPU). The control unit 31 is connected to, through a bus, hardware units constituting the image processing device 3. The main storage unit 32 is a temporary storage area such as a static random access memory (SRAM), a dynamic random access memory (DRAM), and a flash memory, and temporarily stores data required for the control unit 31 to execute an arithmetic process.

The input and output I/F 33 is an interface to which the intravascular inspection device 1 and the fluoroscopic image capturing device 2 are connected and the display device 4 and the input device 5 are connected. The control unit 31 acquires the IVUS image from the intravascular inspection device 1 and the angiogram from the fluoroscopic image capturing device 2 through the input and output I/F 33. The control unit 31 outputs medical image signals of the IVUS image and the angiogram to the display device 4 through the input and output I/F 33 to display the medical images on the display device 4. Further, the control unit 31 receives information input to the input device 5 through the input and output I/F 33.

The auxiliary storage unit 34 is a storage device such as a hard disk, an electrically erasable programmable ROM (EEPROM), or a flash memory. The auxiliary storage unit 34 stores a computer program P executed by the control unit 31 and various types of data required for the process of the control unit 31. In addition, the auxiliary storage unit 34 stores a first learning model M1 described later. The first learning model M1 is a machine learning model trained by predetermined training data, and is a model that receives the IVUS image as an input and outputs regions of the intravascular lumen and the vessel wall in the input IVUS image. The first learning model M1 can be used as a program module constituting artificial intelligence software. The auxiliary storage unit 34 may be an external storage device connected to the image processing device 3. The computer program P may be written in the auxiliary storage unit 34 at a stage of manufacturing the image processing device 3, or the image processing device 3 may acquire a program distributed by a remote server device through communication and store the program in the auxiliary storage unit 34.

The reading unit 35 reads data stored in a recording medium 30 such as a compact disc (CD), a digital versatile disc (DVD), or a universal serial bus (USB) memory. The computer program P may be readably recorded in the recording medium 30, or may be read by the reading unit 35 from the recording medium 30 and stored in the auxiliary storage unit 34. The computer program P may be recorded in a semiconductor memory, and the control unit 31 may read the computer program P from the semiconductor memory and execute the computer program P.

The image processing device 3 may be a multi-computer including a plurality of computers. In addition, the image processing device 3 may be a server client system, a cloud server, or a virtual machine virtually constructed by software. In the following description, the image processing device 3 will be described as one computer.

In the image processing device 3 according to the present embodiment, the control unit 31 reads out and executes the computer program P stored in the auxiliary storage unit 34 to execute a process of compensating a framed out region (missing region) for the IVUS image in which the blood vessel is framed out, among the IVUS images captured by the intravascular inspection device 1. Accordingly, the image processing device 3 according to the present embodiment can provide the IVUS image in which the missing region of the blood vessel is compensated. The image processing device 3 according to the present embodiment uses the first learning model M1 when specifying the IVUS image in which the blood vessel is framed out.

Figure 4A:
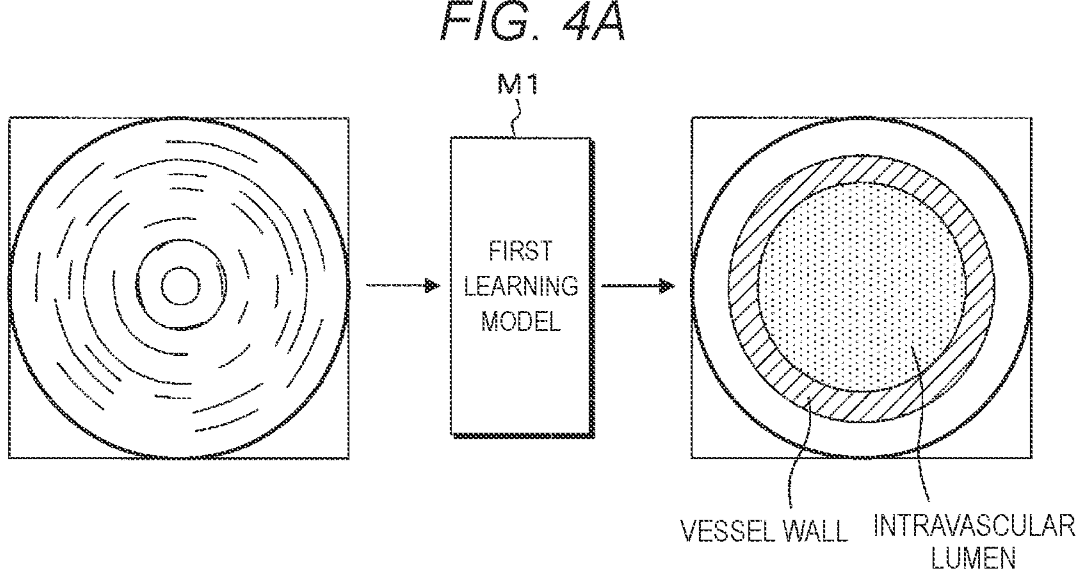
FIG. 4A is a schematic diagram showing an outline of a first learning model.
Figure 4B:
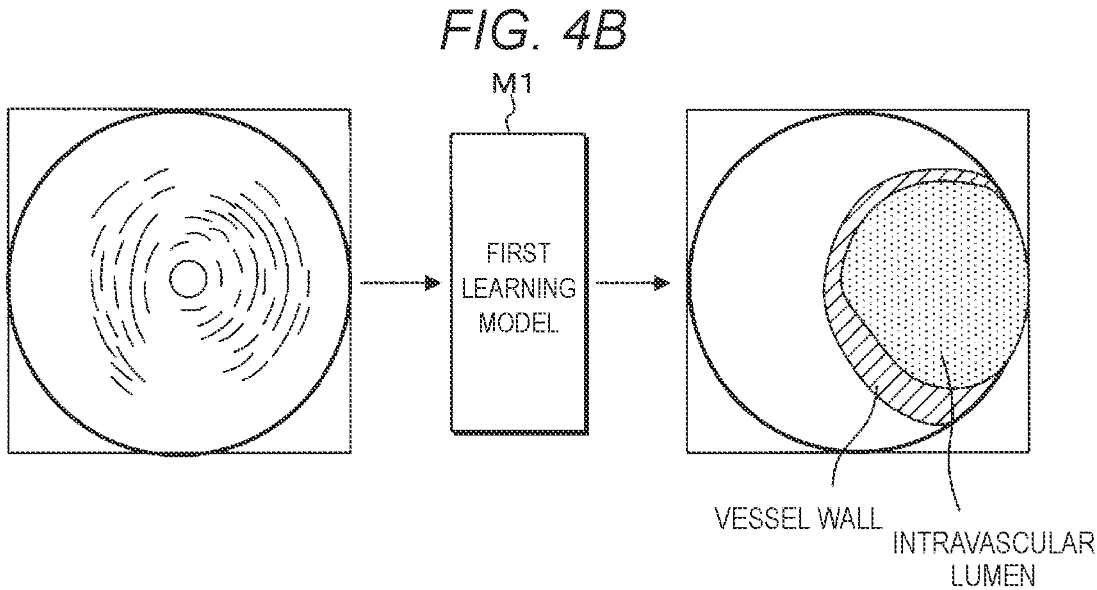
FIG. 4B is a schematic diagram showing the outline of the first learning model.

FIGS. 4A and 4B are schematic diagrams showing an outline of the first learning model M1. The first learning model M1 is a model that recognizes a predetermined object in the IVUS image. The first learning model M1 is a model capable of classifying objects in an image in units of pixels by an image recognition technique using, for example, semantic segmentation. The first learning model M1 according to the present embodiment can be a machine learning model that was trained to receive one sheet of the IVUS image as an input and recognize the intravascular lumen and the vessel wall in the IVUS image, and outputs a recognition result. Specifically, the first learning model M1 classifies pixels of the input IVUS image into an intravascular lumen region, a vessel wall region, and other regions, and outputs a classified IVUS image in which a label of each region is associated with respective pixels (hereinafter, referred to as a label image). The first learning model M1 can be implemented by, for example, U-Net, a fully convolutional network (FCN), or SegNet (semantic segmentation model).

The first learning model M1 can include an input layer, an intermediate layer, and an output layer. The intermediate layer can include a convolutional layer, a pooling layer, and a deconvolutional layer. The convolutional layer generates a feature map by extracting a feature of an image from pixel information of the image input through the input layer, and the pooling layer compresses the generated feature map. The deconvolutional layer enlarges (maps) the feature map generated by the convolutional layer and the pooling layer to an original image size. The deconvolutional layer identifies which object is present at which position in the image in units of pixels based on the feature extracted by the convolutional layer, and generates a label image indicating which object pixels correspond to. FIGS. 4A and 4B show an example in which the IVUS images shown in FIGS. 2A and 2B are input to the first learning model M1. As shown on right sides in FIGS. 4A and 4B, the label image output from the first learning model M1 is an image in which pixels of the IVUS image are classified into the intravascular lumen region, the vessel wall region, and the other regions, and a pixel value corresponding to each region is assigned. In FIGS. 4A and 4B, the pixel values corresponding to the intravascular lumen region and the vessel wall region are indicated by different hatchings.

The first learning model M1 having the above configuration can be generated by preparing training data including an IVUS image for training and a label image in which data indicating an object to be determined (in this case, an intravascular lumen and a blood vessel wall) is labeled for respective pixels in the IVUS image as shown in right sides in FIGS. 4A and 4B, and performing machine learning on an untrained learning model using the training data. In a training label image, a label representing a coordinate range corresponding to a region of each object and a type of each object is assigned to the IVUS image for training. When the IVUS image in the training data is input, the first learning model M1 learns to output the label image in the training data. Specifically, the first learning model M1 performs arithmetic in the intermediate layer based on the input IVUS image, and acquires a detection result of detecting each object (here, the intravascular lumen and the vessel wall) in the IVUS image. More specifically, the first learning model M1 acquires, as an output, the label image in which a value indicating the type of the classified object is labeled for respective pixels in the IVUS image. Then, the first learning model M1 compares an acquired detection result (label image) with a coordinate range of a correct object region indicated by the training data and a type of the object, and optimizes a parameter such as a weight (coupling coefficient) between neurons such that the detection result approximate to the coordinate range of the correct object region and the type of the object indicated by the training data. A method of optimizing the parameter is not particularly limited, and a gradient descent method, a back propagation method, or the like can be used. Accordingly, when the IVUS image is input, the first learning model M1 that outputs the label image indicating the intravascular lumen region and the vessel wall region in the IVUS image is obtained.

The image processing device 3 prepares the first learning model M1 in advance, and uses the first learning model M1 to detect the intravascular lumen and the vessel wall in the IVUS image. The first learning model M1 only needs to be able to identify a position and a shape of the intravascular lumen and the vessel wall in the IVUS image. The first learning model M1 may be trained in another learning device. The trained first learning model M1 generated by training in the other learning device is downloaded from the learning device to the image processing device 3 through, for example, a network or the recording medium 30, and can be stored in the auxiliary storage unit 34.

Figure 5:
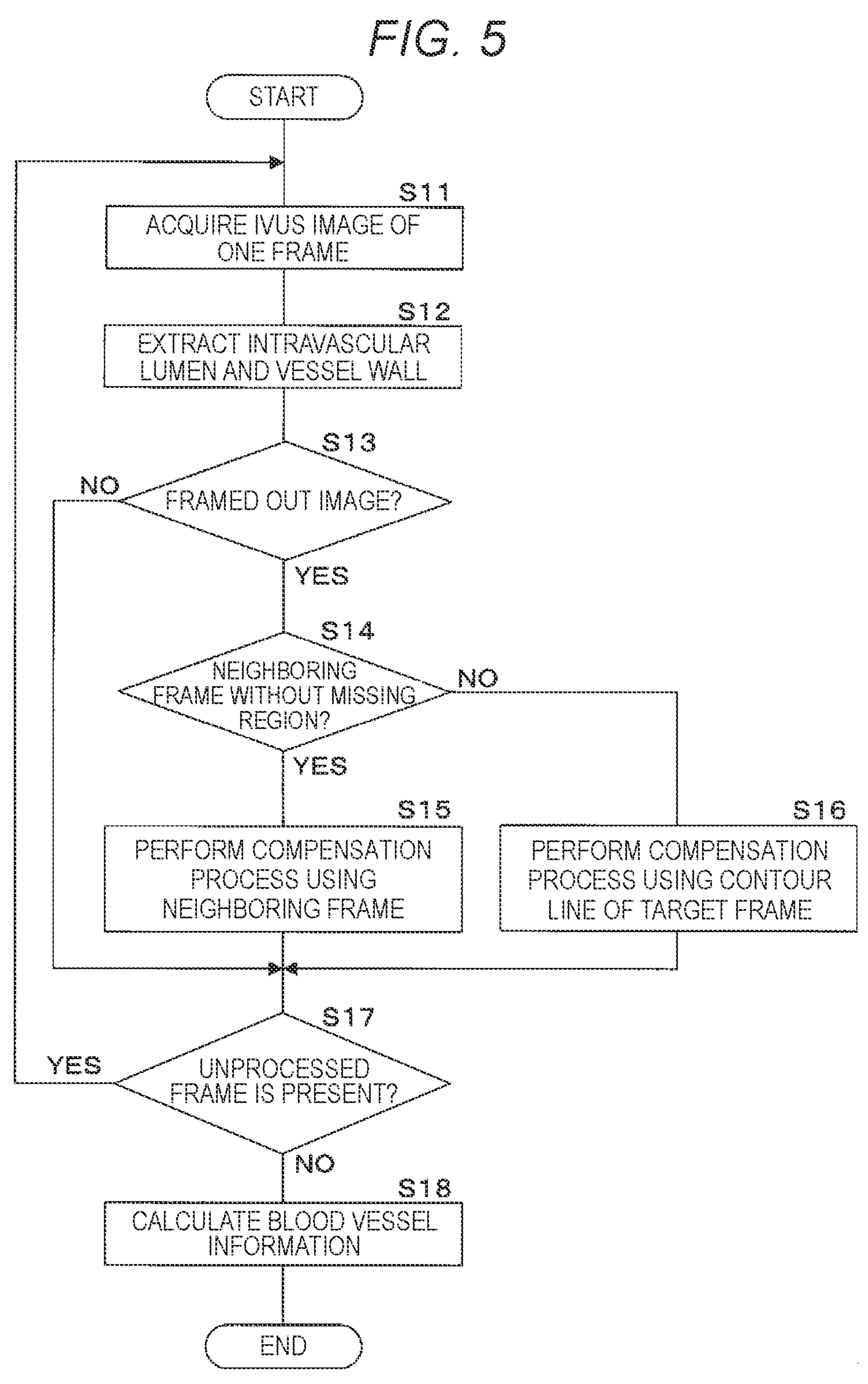
FIG. 5 is a flowchart showing an example of a compensation process procedure for the IVUS image.

Hereinafter, the process of compensating the missing region of the blood vessel for the IVUS image in which the blood vessel is framed out will be described. FIG. 5 is a flowchart showing an example of a compensation process procedure for the IVUS image, and FIGS. 6A to 10 are schematic diagrams showing the compensation process. The following process is performed by the control unit 31 of the image processing device 3 according to the computer program P stored in the auxiliary storage unit 34. The intravascular inspection device 1 performs an imaging process while performing a pullback operation of rotating the ultrasound transmitter and receiver provided in the catheter 1*a* and moving the ultrasound transmitter and receiver at a constant speed along an axial direction (running direction of the blood vessel). The intravascular inspection device 1 acquires a plurality of IVUS images in one pullback operation by continuously performing the imaging process at a predetermined time interval. Accordingly, the image processing device 3 performs the following processes on the plurality of IVUS images acquired in one pullback operation.

The control unit 31 (acquisition unit) of the image processing device 3 acquires one frame (one sheet) of the IVUS image captured by the intravascular inspection device 1 (S11). The IVUS image may be an IVUS image that is already captured by the intravascular inspection device 1 and stored in the main storage unit 32 or the auxiliary storage unit 34, or may be an IVUS image sequentially output from the intravascular inspection device 1.

The control unit 31 performs a process of extracting an intravascular lumen and a vessel wall in the acquired IVUS image (S12). Here, the control unit 31 inputs the IVUS image to the first learning model M1, and specifies regions of the intravascular lumen and the vessel wall in the IVUS image based on the label image output from the first learning model M1. Specifically, when the label image as shown on the right sides of FIGS. 4A and 4B is acquired, the control unit 31 specifies respective contour lines of the regions of the intravascular lumen and the vessel wall indicated by the label image. FIGS. 6A to 6D show examples of the contour lines of the intravascular lumen and the vessel wall, in which broken lines in FIGS. 6A to 6D indicate the contour line of the intravascular lumen (inner surface of the vessel wall), and dashed-dotted lines in FIGS. 6A to 6D indicate the contour line of the vessel wall (outer surface of the vessel wall). In this way, by specifying the regions of the intravascular lumen and the vessel wall in the IVUS image using the first learning model M1 trained by the training data, the intravascular lumen and the vessel wall can be accurately detected. In S11, the control unit 31 may acquire the IVUS image in which the regions of the intravascular lumen and the vessel wall are already extracted using the first learning model M1, and in this case, the process of S12 can be skipped.

The control unit 31 determines whether the IVUS image is a framed out image in which a part of the intravascular lumen or the vessel wall is missing based on the regions of the intravascular lumen and the vessel wall in the extracted IVUS image (S13). For example, the control unit 31 determines whether the contour line of the intravascular lumen intersects the contour line of the IVUS image, determines that a part of the intravascular lumen is missing when the contour line of the intravascular lumen intersects the contour line of the IVUS image, and determines that the intravascular lumen is not missing when no contour line of the intravascular lumen intersects the contour line of the IVUS image. The control unit 31 determines whether the contour line of the vessel wall intersects the contour line of the IVUS image, determines that a part of the vessel wall is missing when the contour line of the vessel wall intersects the contour line of the IVUS image, and determines that the vessel wall is not missing when no contour line of the vessel wall intersects the contour line of the IVUS image. Specifically, in the example shown in FIG. 6A, the contour line of the intravascular lumen and the contour line of the vessel wall both intersect the contour line of the IVUS image, and thus the IVUS image is determined to have both intravascular lumen and vessel wall which are framed out. In the example shown in FIG. 6B, the contour line of the intravascular lumen does not intersect the contour line of the IVUS image, and the contour line of the vessel wall intersects the contour line of the IVUS image, and thus the IVUS image is determined to have only the vessel wall framed out. Through such a process, the control unit 31 functions as an extraction unit that extracts a tomographic image framed out from among a plurality of tomographic images.

Figure 6A:
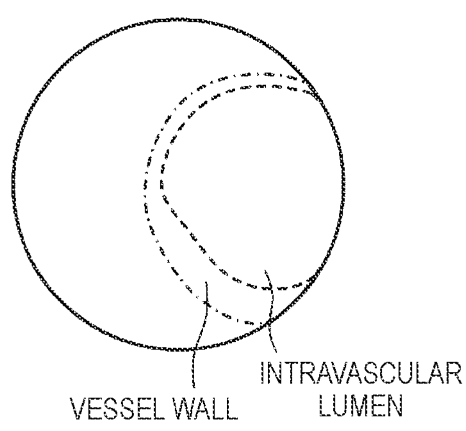
FIG. 6A is a schematic diagram showing a compensation process.
Figure 6B:
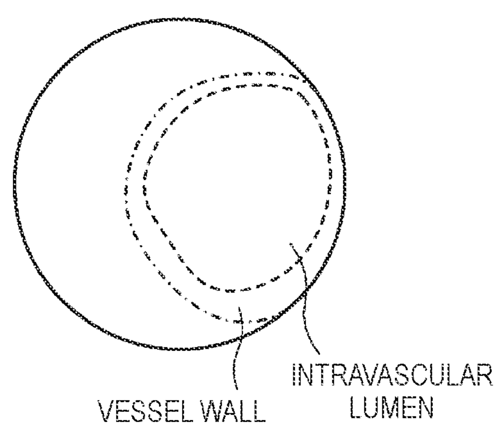
FIG. 6B is a schematic diagram showing the compensation process.
Figure 6C:
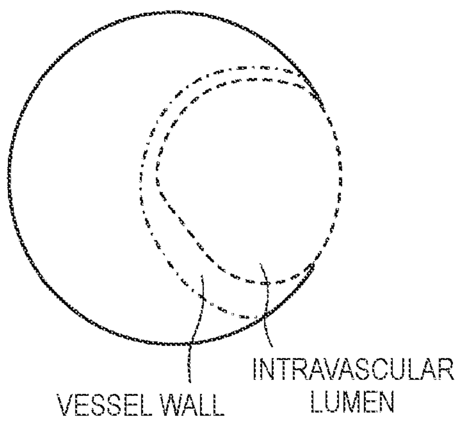
FIG. 6C is a schematic diagram showing the compensation process.
Figure 6D:
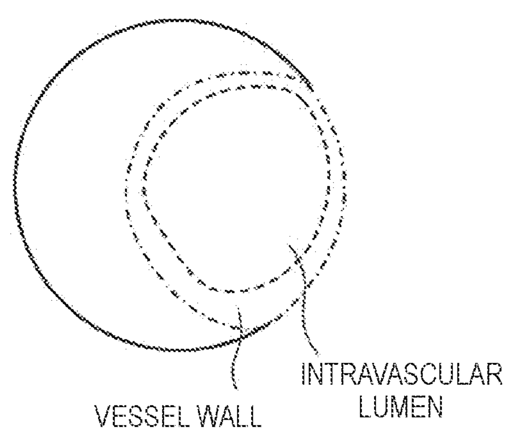
FIG. 6D is a schematic diagram showing the compensation process.

In the first learning model M1, the contour line of the intravascular lumen and the contour line of the vessel wall as shown in FIGS. 6C and 6D can be specified by respectively detecting the intravascular lumen region and the vessel wall region. In FIG. 6C, the contour line of the intravascular lumen is indicated by the broken line, and a broken line portion of the contour line in the IVUS image indicates a contour line overlapping (matching) with the contour line of the intravascular lumen. In FIG. 6C, a part of the contour line of the vessel wall also overlaps a part of the contour line of the IVUS image, but is not shown here to avoid complication of the drawing. In FIG. 6D, the contour line of the vessel wall is indicated by the dashed-dotted line, and a dashed-dotted line portion of the contour line in the IVUS image indicates a contour line overlapping (matching) with the contour line of the vessel wall. In this way, when a part of the intravascular lumen and the vessel wall is missing, a part of the contour lines of the intravascular lumen and the vessel wall overlaps the contour line of the IVUS image. Accordingly, the control unit 31 may determine whether a part of the contour line of the intravascular lumen overlaps the contour line of the IVUS image, determine that a part of the intravascular lumen is missing when the part of the contour line of the intravascular lumen overlaps the contour line of the IVUS image, and determine that the intravascular lumen is not missing when the part of the contour line of the intravascular lumen does not overlap the contour line of the IVUS image. The control unit 31 may determine whether a part of the contour line of the vessel wall overlaps the contour line of the IVUS image, determine that a part of the vessel wall is missing when the part of the contour line of the vessel wall overlaps the contour line of the IVUS image, and determine that the vessel wall is not missing when the part of the contour line of the vessel wall does not overlap the contour line of the IVUS image. Further, the control unit 31 may first determine whether the vessel wall is missing (whether the vessel wall is framed out), and may determine whether the intravascular lumen is missing when the vessel wall is missing. In this case, when the vessel wall is not missing, it is possible to skip the determination of whether the intravascular lumen is missing.

When it is determined that the IVUS image acquired in S11 is the image framed out (S13: YES), the control unit 31 determines whether an image of a neighboring frame is an IVUS image not framed out (an image without a missing region) (S14). Specifically, when only the vessel wall is framed out in the IVUS image of a frame to be processed, the control unit 31 determines whether an image of the neighboring frame is an IVUS image in which the vessel wall is not framed out. When the intravascular lumen and the vessel wall are framed out in the IVUS image of the frame to be processed, the control unit 31 determines whether an IVUS image of a neighboring frame is an IVUS image in which the intravascular lumen and the vessel wall are not framed out. The IVUS image is captured while the ultrasound transmitter and receiver provided in the catheter 1*a* is pulled from a position far from the intravascular inspection device 1 (distal portion) by a pullback operation. Accordingly, a thickness of the blood vessel at an imaging start position is relatively small (outer diameter is small), and the thickness of the blood vessel tends to increase as the ultrasound transmitter and receiver moves. Therefore, it is expected that the IVUS image is not framed out before the IVUS image in which the blood vessel is framed out.

Figure 7:
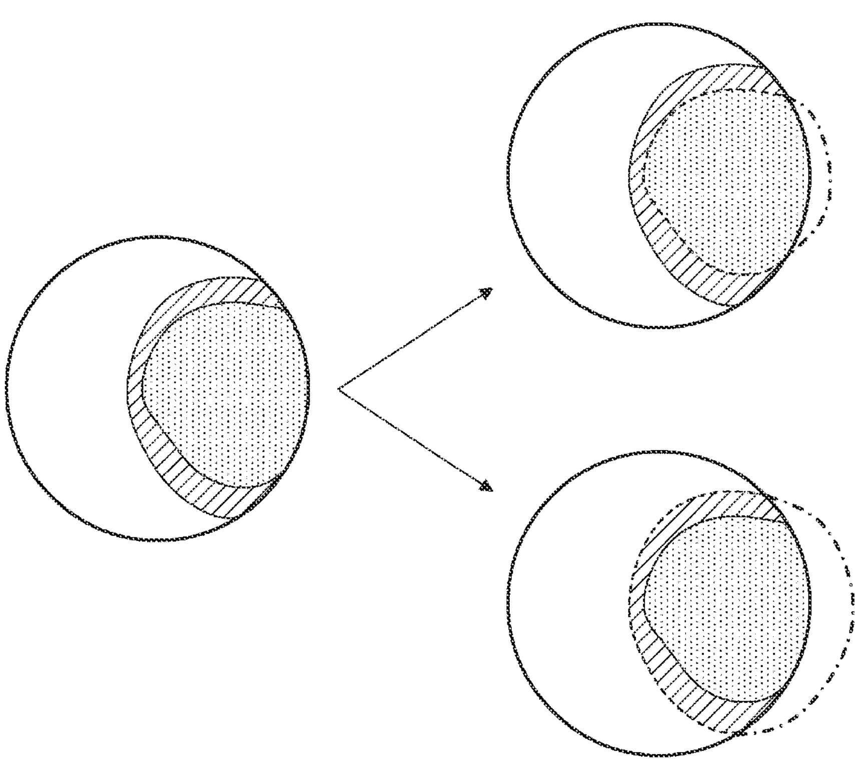
FIG. 7 is a schematic diagram showing the compensation process.

When it is determined that the image of the neighboring frame is the IVUS image framed out (S14: NO), the control unit 31 (compensation unit) performs a process of compensating the missing region which is framed out using the contour line which is not framed out in the IVUS image of the frame to be processed (target frame) (S16). FIG. 7 shows the process of compensating the missing region of the intravascular lumen based on the contour line of the intravascular lumen and compensating the missing region of the vessel wall based on the contour line of the vessel wall in the IVUS image in which the intravascular lumen and the vessel wall are framed out. A left side in FIG. 7 shows an IVUS image in which the contour lines of the intravascular lumen and the vessel wall are specified, upper right in FIG. 7 shows a state in which a missing contour line of the intravascular lumen is compensated, and lower right in FIG. 7 shows a state in which a missing contour line of the vessel wall is compensated. When the intravascular lumen and the vessel wall are framed out, the control unit 31 first compensates the missing region of the intravascular lumen. For example, the control unit 31 compensates the contour line of the missing region by a spline or the like based on the contour line of the intravascular lumen which is not missing for the frame to be processed. Specifically, the control unit 31 calculates a parameter in a spline function based on the contour line, which is not missing, and compensates the contour line of the missing region using the calculated spline function. In the upper right in FIG. 7, the contour line which is not missing is indicated by the broken line, and the contour line of the missing region as indicated by the dashed-dotted line is compensated by the spline function based on the contour line. Similarly, the control unit 31 compensates the contour line of the missing region of the vessel wall based on the contour line of the vessel wall which is not missing. Accordingly, as shown in the lower right in FIG. 7, the contour line of the missing region of the vessel wall as shown by the dashed-dotted line is compensated by the spline function based on the contour line (broken line portion) of the vessel wall which is not missing.

When both the intravascular lumen and the vessel wall are missing, either a compensation process for the intravascular lumen or a compensation process for the vessel wall may be performed first. Under a condition that the compensated contour line of the vessel wall is outside (not inside) the compensated contour line of the intravascular lumen, the compensation processes are executed. The compensation (compensation) of the contour lines of the intravascular lumen and the vessel wall is not limited to being performed by the above process. For example, the control unit 31 may calculate a radius of curvature of a circle approximating the contour line and a center position of the circle having the radius of curvature based on the contour line of the intravascular lumen which is not missing, and compensate the contour line of the missing region of the intravascular lumen based on the calculated center position and radius of curvature. Similarly, the control unit 31 may calculate a radius of curvature and a center position of a circle approximating the contour line based on the contour line of the vessel wall, which is not missing, and compensate the contour line of the missing region of the vessel wall based on the calculated center position and radius of curvature.

Figure 8:
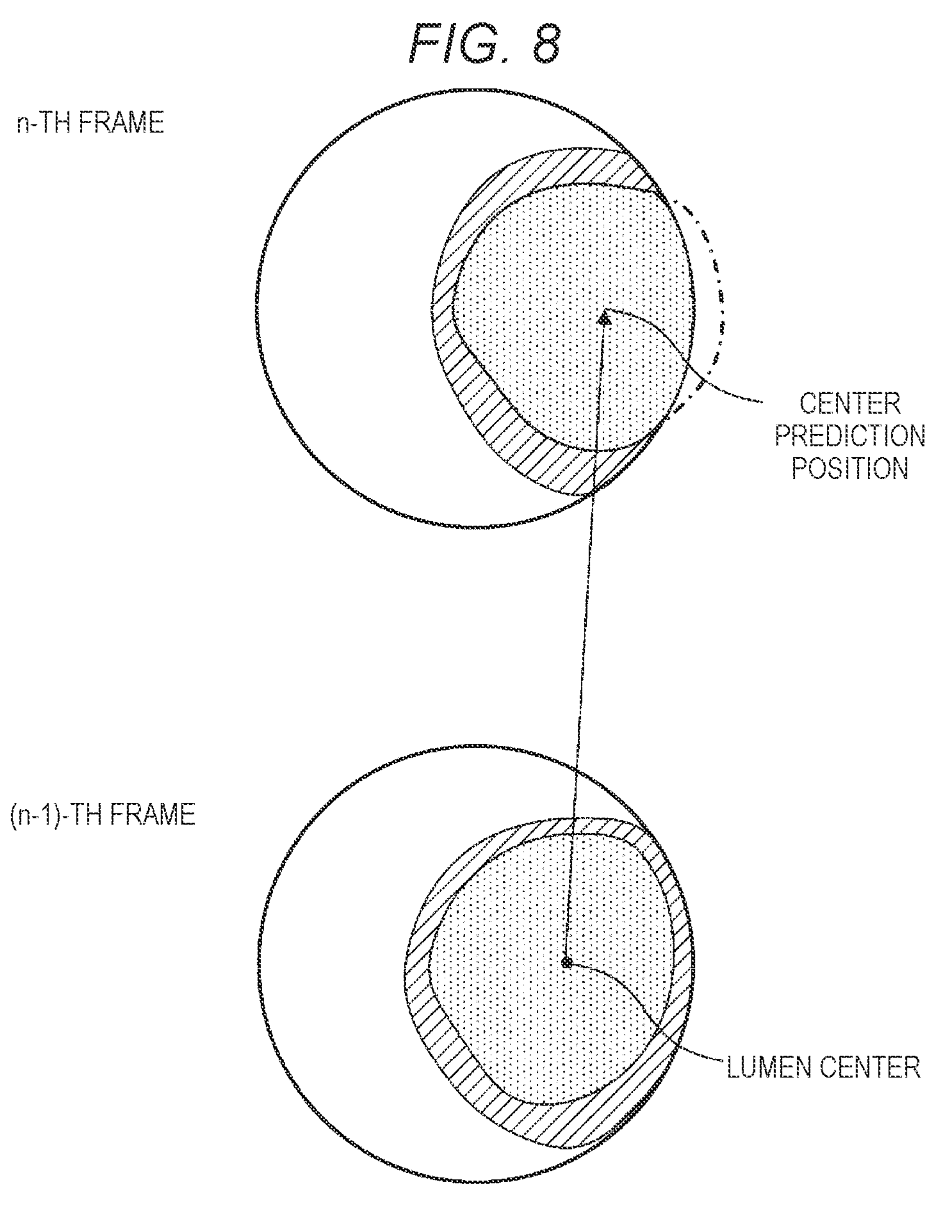
FIG. 8 is a schematic diagram showing the compensation process.

When it is determined that the image of the neighboring frame is the IVUS image not framed out (S14: YES), the control unit 31 (compensation unit) performs a process of compensating the missing region in the IVUS image which is framed out using the IVUS image of the neighboring frame (S15). FIG. 8 shows a process of compensating a missing region of the intravascular lumen in an IVUS image of an n-th frame when an intravascular lumen in an IVUS image of an (n−1)-th frame is not framed out and the intravascular lumen in the IVUS image of the n-th frame is framed out. The control unit 31 first specifies a center position of the intravascular lumen based on the contour line of the intravascular lumen in the IVUS image of the (n−1)-th frame that is not framed out. Then, the control unit 31 predicts a center position of the intravascular lumen in the n-th frame based on the contour line and the center position of the intravascular lumen in the (n−1)-th frame and the contour line of the intravascular lumen in the n-th frame. Since the contour lines of the intravascular lumen are similar in the IVUS images adjacent to each other in time series, the control unit 31 can predict the center position of the intravascular lumen in the n-th frame by overlapping the contour line of the intravascular lumen in the (n−1)-th frame with the contour line of the intravascular lumen in the n-th frame. The control unit 31 compensates the missing region (missing contour line) of the intravascular lumen in the n-th frame based on the predicted center position. Here, the control unit 31 may calculate the radius of curvature of the circle approximating the contour line in the intravascular lumen in the n-th frame based on the contour line, which is not missing and the predicted center position, and compensate the contour line of the missing region based on the calculated radius of curvature and the predicted center position. The control unit 31 may predict the contour line of the intravascular lumen in the n-th frame from the contour line of the intravascular lumen in the (n−1)-th frame without predicting the center position of the intravascular lumen in the n-th frame and compensate the contour line in a blood vessel region. Accordingly, the contour line of the intravascular lumen in the n-th frame is compensated as indicated by the dashed-dotted line in FIG. 8.

Similarly, the control unit 31 compensates the contour line of the vessel wall in the IVUS image of the n-th frame in which the vessel wall is framed out based on the IVUS image of the (n−1)-th frame in which the vessel wall is not framed out. In an example shown in FIG. 8, since the vessel wall in the IVUS image of the (n−1)-th frame is also framed out, the compensation process of the vessel wall in the IVUS image of the n-th frame is not performed based on the IVUS image of the (n−1)-th frame. In this case, for example, by the process of S16, the compensation process of the missing region of the vessel wall may be performed based on the contour line of the vessel wall in the target frame (n-th frame). For example, the compensation process of the vessel wall in the IVUS image of the n-th frame may be performed based on the IVUS image in which the vessel wall is not framed out before an (n−2)-th frame. When the contour line of the vessel wall is compensated based on the IVUS image of the (n−2)-th frame for the IVUS image of the (n−1)-th frame (when the center position of the vessel wall is predicted), the compensation process of the vessel wall in the IVUS image of the n-th frame may be performed using the compensated contour line (predicted center position).

When the control unit 31 determines that the IVUS image is not the framed out image in step S13 (S13: NO), the process skips S14 to S16 and proceeds to S17. After the process of S15 or S16, the control unit 31 determines whether a frame (IVUS image) in which the above process is not executed is present among IVUS images of a plurality of frames acquired in one pullback operation (S17). When it is determined that the unprocessed frame is present (S17: YES), the control unit 31 returns to the process of S11 and executes the above processes of S11 to S16 on the unprocessed frame. Accordingly, it is determined whether the intravascular lumen or the vessel wall is framed out for the IVUS image of each frame, and when the intravascular lumen or the vessel wall is framed out, the contour line of the missing region can be compensated.

The control unit 31 compensates the missing region for the IVUS image framed out as described above, and then calculates blood vessel information relating to the blood vessel imaged in the IVUS image based on the IVUS image which is not framed out and the compensated IVUS image (S18). The blood vessel information can include, for example, intravascular lumen information, vessel wall information, and plaque information. The intravascular lumen information can include, for example, as indicated by solid arrows in FIG. 9A, a minimum value of an inner diameter of the blood vessel passing through the center of the intravascular lumen (minimum lumen diameter: MinLD) and a maximum value (maximum lumen diameter: MaxLD), and further can include a cross-sectional area of the intravascular lumen (the cross-sectional area of a region surrounded by the contour line) (lumen cross-sectional area: Lumen CSA). The blood vessel information can include an eccentricity of the intravascular lumen (lumen eccentricity) calculated from the minimum value (MinLD) and the maximum value (MaxLD) of the inner diameter of the blood vessel. The eccentricity of the intravascular lumen is calculated using an expression, for example, {(MaxLD—MinLD)/MaxLD}. The blood vessel information further includes a cross-sectional area of a control portion (reference lumen CSA) in a section in which the ultrasound transmitter and receiver moved by the pullback operation, for example, a cross-sectional area of the intravascular lumen imaged on the distal end of the catheter 1*a* (cross-sectional area of the distal portion), a cross-sectional area of the intravascular lumen imaged on a proximal end of the catheter 1*a* (cross-sectional area of a proximal portion), a maximum cross-sectional area in the section, and an average cross-sectional area in the section. Further, the blood vessel information can include a degree of stenosis of the intravascular lumen (lumen area stenosis) calculated from the cross-sectional area of each control portion.

The vessel wall information can include a cross-sectional area of an external elastic membrane (EEM) (EEM CSA) calculated as the cross-sectional area of the blood vessel, and cross-sectional areas of a plaque and a middle membrane (plaque plus media CSA) calculated from the cross-sectional area of the blood vessel. The cross-sectional areas of the plaque and middle membrane are calculated using an expression, for example, (EEM CSA−lumen CSA). The vessel wall information can include, for example, a minimum value and a maximum value of an outer diameter of the blood vessel passing through the center of the blood vessel, as indicated by broken line arrows in FIG. 9A.

The plaque information can include a minimum value of a distance (minimum plaque plus media thickness) and a maximum value of the distance (maximum plaque plus media thickness) from an outer edge of the intravascular lumen to an outer edge of the blood vessel on a straight line passing through the center of the intravascular lumen, and further can include an eccentricity of the plaque (plaque plus media eccentricity). The eccentricity of the plaque is calculated by using an expression, for example, {(maximum plaque plus media thickness−minimum plaque plus media thickness)/maximum plaque plus media thickness}. The plaque information includes an index of a plaque volume (plaque plus media burden), and the index of the plaque volume is calculated by using an expression, for example, (plaque plus media CSA/EEM CSA).

When the IVUS image is captured after a stent is placed in a stenosis site, the blood vessel information calculated based on the IVUS image may include stent information. The stent information may include a cross-sectional area of a region surrounded by the stent (state CSA), and a minimum diameter of the stent (minimum stent diameter) and a maximum diameter of the stent (maximum stent diameter) passing through a center of the stent. The stent information may also include stent symmetry calculated using the minimum diameter and the maximum diameter of the stent. The stent symmetry is calculated using an expression, for example, {(maximum diameter−minimum diameter)/maximum diameter}. Further, the stent information may also include a ratio of the minimum value of the cross-sectional area of the stent to the cross-sectional area of the control portion, which is calculated using a minimum value of the cross-sectional area of the stent (minimum stent CSA). The ratio is calculated using an expression, for example, (minimum value of cross-sectional area of stent/cross-sectional area of control portion).

Further, the blood vessel information calculated based on the IVUS image may include a measurement amount of calcification in the plaque. The measurement amount of calcification in the plaque is represented by a numerical value of, for example, ¼ or less or ¼ to ½ with respect to the blood vessel (360° one round) with the center of the intravascular lumen or the center of the catheter 1*a* (that is, the center of the IVUS image) as a measurement center. It may be switchable by the operator whether the center of the intravascular lumen or the center of the catheter 1*a* is used as the measurement center. Since the calculation process of each piece of the information described above is a process executed by the intravascular inspection device 1 or the image processing device 3 which is used in the related art, a detailed description of the processes executed by the intravascular inspection device 1 of the image processing device 3 will be omitted. When calculating the blood vessel information as described above, the control unit 31 displays the blood vessel information on the display device 4 to present the blood vessel information to the operator.

Figure 9A:
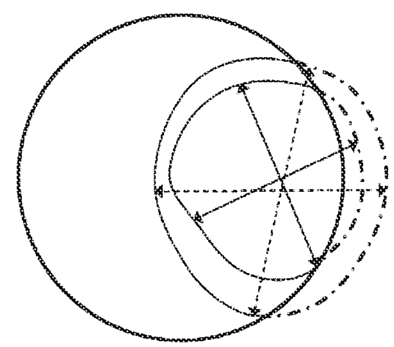
FIG. 9A is a schematic diagram showing the compensation process.
Figure 9B:
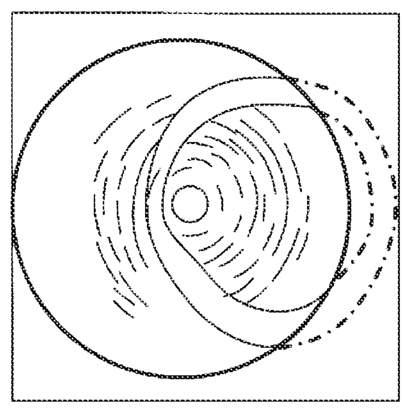
FIG. 9B is a schematic diagram showing the compensation process.

In addition to calculating the information relating to the blood vessel as described above, the control unit 31 may generate a display screen that displays an IVUS image in which the contour line of the intravascular lumen or the vessel wall that is framed out is compensated for the IVUS image in which the intravascular lumen or the vessel wall is framed out. FIG. 9B shows a state in which the contour lines of the missing regions (the intravascular lumen and the vessel wall) are compensated for the IVUS image in which the intravascular lumen and the vessel wall are framed out. In a screen shown in FIG. 9B, the contour lines of the intravascular lumen and the vessel wall that are not framed out are indicated by solid lines, and the contour lines of the compensated missing regions are indicated by dashed-dotted lines. As shown in FIG. 9B, by displaying (adding) the compensated contour lines in a mode different from that of the contour lines that are not framed out, a compensated place region (contour lines) can be explicitly presented.

Figure 10:
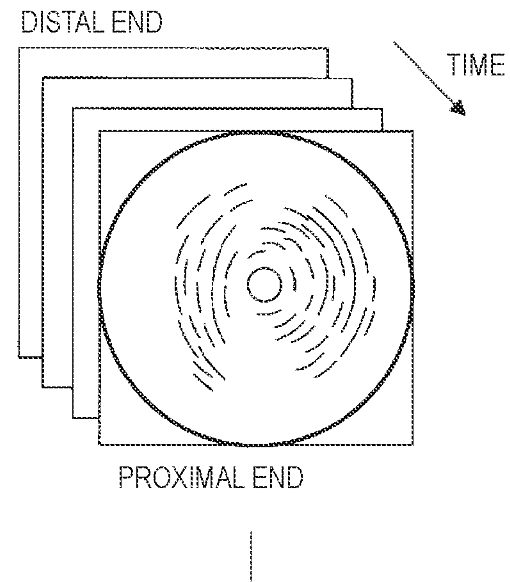
FIG. 10 is a schematic diagram showing the compensation process.
Figure 10:
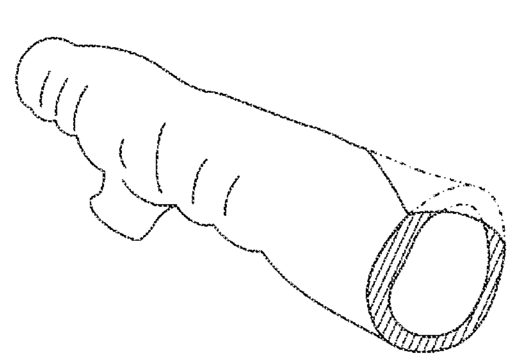

Further, the control unit 31 may generate a three-dimensional image of the blood vessel imaged in the IVUS image based on the IVUS image in which the missing region is compensated. The IVUS images captured continuously can be used to generate the three-dimensional image. Therefore, the control unit 31 may generate the three-dimensional image of the blood vessel imaged in the IVUS image by binding the IVUS image in which the intravascular lumen and the vessel wall are not framed out and the IVUS image in which the missing region is compensated in an imaging order. The three-dimensional image can be generated by, for example, a voxel method. The three-dimensional image is voxel data represented by a coordinate value of a voxel in a predetermined coordinate system and a voxel value indicating the type of the object. A data format of the three-dimensional image is not particularly limited, and may be polygon data or point cloud data. FIG. 10 shows a three-dimensional image in which the IVUS images of a plurality of frames captured by one pullback operation are combined in an imaging order. An example shown in FIG. 10 shows a state in which the intravascular lumen and the vessel wall are framed out in the IVUS image captured on the proximal end of the catheter 1*a* and the framed out missing region is compensated in the three-dimensional image. In a screen shown in FIG. 10, the contour line of the compensated missing region is indicated by the dashed-dotted line. Also in this case, as shown in FIG. 10, the contour line of the compensated missing region is displayed in a mode different from the contour line which, is not framed out, whereby the framed out region can be explicitly presented.

In the present embodiment, when the intravascular lumen or the vessel wall is framed out in the IVUS image captured by the intravascular inspection device 1, the framed out region (missing region) can be compensated. Accordingly, a state in the blood vessel can be appropriately observed based on the compensated IVUS image. A size of the intravascular lumen, a thickness of the vessel wall, and the like can be accurately calculated based on the compensated IVUS image. The contour lines of the intravascular lumen and the vessel wall having a shape close to a circle can be accurately compensated by compensating the contour lines of the intravascular lumen and the vessel wall which are framed out based on the contour lines of the intravascular lumen and the vessel wall which are not framed out in the target frame. When the contour line of the blood vessel region is compensated based on the contour lines of the intravascular lumen and the vessel wall in frames adjacent to each other in time series, it is possible to perform the compensation process with a relatively higher accuracy.

In the present embodiment, with respect to the IVUS image captured by the intravascular inspection device 1, when the intravascular lumen or the vessel wall is framed out, the image processing device 3 compensates the framed out missing region. In addition, when the intravascular inspection device 1 captures an OCT image, the image processing device 3 may compensate a framed out missing region (an intravascular lumen and a vessel wall) for the OCT image in which the intravascular lumen or the vessel wall is framed out.

In the present embodiment, a process of extracting the intravascular lumen and the vessel wall in the tomographic image (for example, the IVUS image) may use the first learning model M1, or may be performed based on a rule. In the present embodiment, the image processing device 3 locally performs the process of detecting the regions of the intravascular lumen and the vessel wall in the IVUS image using the first learning model M1, but the disclosure is not limited to the configuration. For example, a server which performs the process of detecting the intravascular lumen and the vessel wall using the first learning model M1 may be provided. In this case, the image processing device 3 may transmit the IVUS image to the server and acquire the regions of the intravascular lumen and the vessel wall in the IVUS image specified by the server. Even in a case of such a configuration, the same process as in the present embodiment can be performed, and the same effect can be obtained.

Embodiment 2

The image diagnosis apparatus 100 will be described, which executes, using a learning model, a process of compensating a framed out region (missing region) for an IVUS image in which an intravascular lumen or a vessel wall is framed out. The image diagnosis apparatus 100 according to the present embodiment can be implemented by devices similar to the devices in the image diagnosis apparatus 100 according to Embodiment 1, and thus the description of the similar configuration will be omitted. In the image diagnosis apparatus 100 according to the present embodiment, the image processing device 3 stores a second learning model M2 (second learning model) in the auxiliary storage unit 34 in addition to the configuration of the image processing device 3 according to Embodiment 1 shown in FIG. 3.

Figure 11:
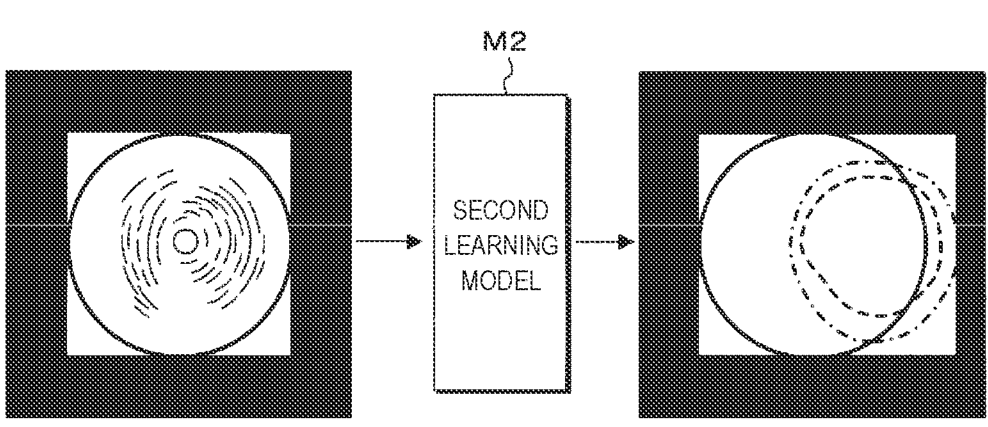
FIG. 11 is a schematic diagram showing an outline of a second learning model.

FIG. 11 is a schematic diagram showing an outline of the second learning model M2. The second learning model M2 is a machine learning model trained by predetermined training data, and is a model that receives an IVUS image in which an intravascular lumen or a vessel wall is framed out as an input and outputs an IVUS image in which a missing region of the intravascular lumen or the vessel wall in the input IVUS image is compensated. The second learning model M2 can be used as a program module constituting artificial intelligence software. For example, as shown in FIG. 11, the second learning model M2 outputs an image indicating contour lines of the intravascular lumen and the vessel wall in the input IVUS image. The second learning model M2 may output the IVUS image obtained by adding the contour lines of the intravascular lumen and the vessel wall to the input IVUS image. As shown in FIG. 11, as the IVUS image input to the second learning model M2, for example, an IVUS image obtained by performing a padding process of adding black pixels or the like to a predetermined region around the IVUS images shown in FIGS. 2A and 2B is used. The region to which the black pixels are added is a region in which the intravascular lumen or the vessel wall can be compensated, and by inputting the IVUS image including such a region to the second learning model M2, the second learning model M2 can output the IVUS image in which the missing region of the intravascular lumen or the vessel wall is compensated.

The second learning model M2 can be implemented by, for example, a convolutional neural network (CNN), the U-Net, a generative adversarial network (GAN), or Cycle-GAN. The second learning model M2 may use another algorithm or may combine a plurality of algorithms.

The second learning model M2 can be, for example, a trained model that recognizes the contour lines of the intravascular lumen and the vessel wall in the input IVUS image in units of pixels. Specifically, the second learning model M2 classifies pixels of the input IVUS image into pixels on the contour line of the intravascular lumen, pixels on the contour line of the vessel wall, and other pixels, and outputs a classified IVUS image in which a label for each classification is associated with respective pixels (referred to as a label image). The second learning model M2 can include, for example, an intermediate layer having a convolutional layer, a pooling layer, and a deconvolutional layer. In the IVUS image input to the second learning model M2, a feature map is generated by the convolutional layer and the pooling layer from pixel information of the image. The deconvolutional layer enlarges (maps) the feature map generated by the convolutional layer and the pooling layer to an original image size. At this time, the deconvolutional layer identifies whether pixels in the image are the pixels on the contour line of the intravascular lumen, the pixels on the contour line of the vessel wall, or the other pixels based on a feature extracted by the convolutional layer. A predetermined value (pixel value) is given to respective pixels identified as the pixels on the contour line of the intravascular lumen or the pixels on the contour line of the vessel wall, and a predetermined value is also given to pixels at a position corresponding to the contour line of the missing region to generate the label image (IVUS image for output). FIG. 11 shows the pixels on the contour line of the intravascular lumen by a broken line, and the pixels on the contour line of the vessel wall by a dashed-dotted line. FIG. 11 shows the label image in which the contour lines of the intravascular lumen and the vessel wall are shown, but a label image may be output in which only the contour line of the missing region of the intravascular lumen or the vessel wall is shown. FIG. 11 shows the label image in which the black pixels are added to the region around the IVUS image including the compensated missing region, but the invention is not limited to such a configuration.

The second learning model M2 having the above configuration can be generated by preparing training data including the captured IVUS image in which the intravascular lumen or the vessel wall is framed out and an IVUS image that is not framed out, and performing machine learning on an untrained learning model using the training data. For example, an image created from the IVUS image which is not framed out may be used as the IVUS image which is framed out. As the IVUS image, which is not framed out for training, a label image in which data indicating the contour line of the intravascular lumen or the vessel wall is labeled for respective pixels on the contour line of the intravascular lumen or the vessel wall in the image is used. In the label image for training, a label indicating a coordinate range corresponding to a contour line of the compensated intravascular lumen or vessel wall and a type of the intravascular lumen or the vessel wall is given to the IVUS image for training (framed out IVUS image). When the IVUS image in the training data is input, the second learning model M2 learns to output the label image in the training data. Specifically, the second learning model M2 performs arithmetic in the intermediate layer based on the input IVUS image, and acquires a detection result of detecting the contour lines of the intravascular lumen and the vessel wall in the IVUS image. More specifically, the second learning model M2 acquires, as an output, a label image in which a value indicating a classification result classified into the contour line of the intravascular lumen or the vessel wall is labeled for respective pixels in the IVUS image. Then, the second learning model M2 compares the acquired label image with a correct label image in the training data, and optimizes a parameter such as a weight (coupling coefficient) between neurons such that the label images approximate to each other. A method of optimizing the parameter is not particularly limited, and for example, a gradient descent method, a back propagation method, or the like can be used. Accordingly, when the IVUS image is input, the second learning model M2 that outputs the label image indicating the contour lines (including the compensated contour lines) of the intravascular lumen and the vessel wall in the IVUS image is obtained.

The image processing device 3 prepares the second learning model M2 in advance, and uses the second learning model M2 to compensate the missing region of the intravascular lumen or the vessel wall in the IVUS image. The second learning model M2 may be any model as long as the second learning model M2 can compensate the contour line of the missing region of the intravascular lumen or the vessel wall in the IVUS image. The second learning model M2 may be trained by another learning device. When trained in the other learning device, the learned second learning model M2 is downloaded from the learning device to the image processing device 3 through, for example, a network or the recording medium 30, and can be stored in the auxiliary storage unit 34.

Figure 12:
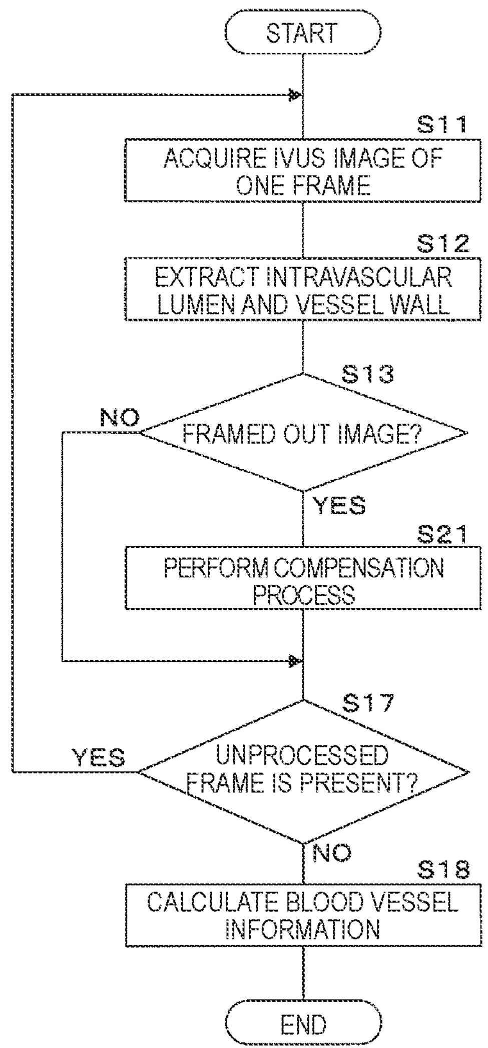
FIG. 12 is a flowchart showing an example of a compensation process procedure according to Embodiment 2.

FIG. 12 is a flowchart showing an example of a compensation process procedure according to Embodiment 2. In a process shown in FIG. 12, S21 is added instead of S14 to S16 in the process shown in FIG. 5. Description of the same steps or processes as those in FIG. 5 is omitted. In the image processing device 3 according to the present embodiment, the control unit 31 performs the processes of S11 to S13 shown in FIG. 5. Accordingly, it is determined whether the intravascular lumen or the vessel wall in the IVUS image is framed out.

When the control unit 31 according to the present embodiment determines that the IVUS image is the image framed out in S13 (S13: YES), the control unit 31 performs a compensation process of the missing region on the IVUS image to be processed using the second learning model M2 (S21). Here, the control unit 31 inputs the IVUS image to be processed to the second learning model M2, and compensates the missing region of the intravascular lumen or the vessel wall in the IVUS image to be processed based on the label image output from the second learning model M2. The control unit 31 may generate the IVUS image in which the missing region is compensated by, for example, overlapping the label image as shown in FIG. 11 with the IVUS image to be processed.

After the process of S21, the control unit 31 executes the process of S17 and thereafter. According to the above processes, also in the present embodiment, it is possible to determine whether the intravascular lumen or the vessel wall is framed out for the IVUS image of each frame, and when the intravascular lumen or the vessel wall is framed out, it is possible to generate the IVUS image in which the contour line of the missing region is compensated. Accordingly, the IVUS image can be presented to an operator, in which the missing region is compensated and a state in the blood vessel is relatively easily observed.

In the present embodiment, the same effect as in the above embodiment can be obtained. In the present embodiment, the second learning model M2 is used to execute the process of compensating the missing region for the IVUS image in which the intravascular lumen or the vessel wall is framed out. Accordingly, by causing the second learning model M2 to accurately learn, the missing region can be accurately compensated for the IVUS image. Also in the present embodiment, modifications appropriately described in the above embodiment can be applied.

Figure 13:
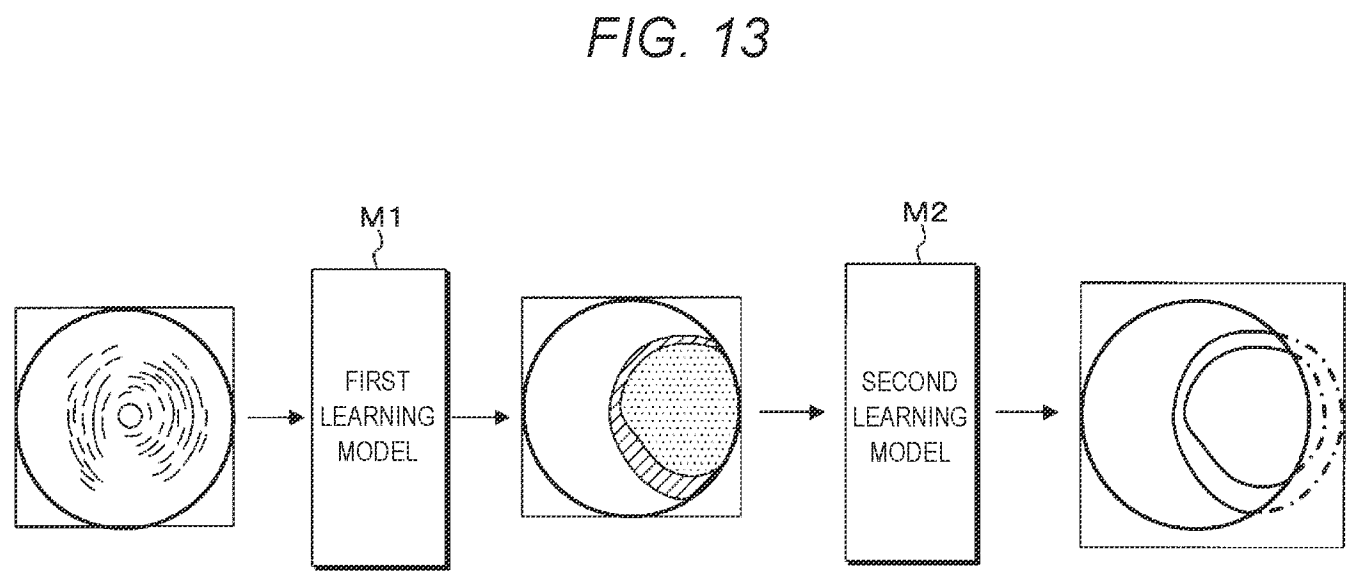

FIG. 13 is a schematic diagram showing a modification of the second learning model M2. As shown in FIG. 13, for example, the second learning model M2 may receive the label image (the image indicating the regions of the intravascular lumen and the vessel wall) output from the first learning model M1 as an input and output an image in which the missing region of the intravascular lumen or the vessel wall is compensated for the input label image. In this case, for example, in the process shown in FIG. 12, the label image obtained by the control unit 31 inputting the IVUS image to the first learning model M1 in step S12 can be input to the second learning model M2 in step S21. Also in this case, based on the label image output from the second learning model M2, an image in which the missing region of the intravascular lumen or the vessel wall in the IVUS image to be processed is compensated is obtained.

Embodiment 3

The image diagnosis apparatus 100 will be described, which takes into consideration whether an imaging position of an IVUS image is a place in which there is a relatively high possibility that an intravascular lumen or a vessel wall is framed out based on a fluoroscopic image (for example, an angiogram) captured by the fluoroscopic image capturing device 2. The image diagnosis apparatus 100 according to the present embodiment can be implemented by devices similar to the devices in the image diagnosis apparatus 100 according to Embodiment 1, and thus the description of the similar configuration will be omitted.

In the image diagnosis apparatus 100 according to the present embodiment, the imaging position of the IVUS image captured by the intravascular inspection device 1 is associated with a position of a blood vessel in the angiogram captured by the fluoroscopic image capturing device 2. Accordingly, the image processing device 3 determines whether there is a possibility that the intravascular lumen or the vessel wall in the IVUS image is framed out in consideration of a thickness of the blood vessel at the position in the angiogram corresponding to the position in which the IVUS image to be processed is captured. For example, when the imaging position of the IVUS image is a place close to a place in which a coronary artery is connected to a major artery, it is determined that there is the possibility that the intravascular lumen or the vessel wall is framed out. When the image processing device 3 according to the present embodiment determines that there is the possibility that the intravascular lumen or the vessel wall is framed out based on the imaging position of the IVUS image, the image processing device 3 executes a determination process of whether the intravascular lumen or the vessel wall is actually framed out, and the compensation process of the missing region is performed when the intravascular lumen or the vessel wall is framed out.

Figure 14:
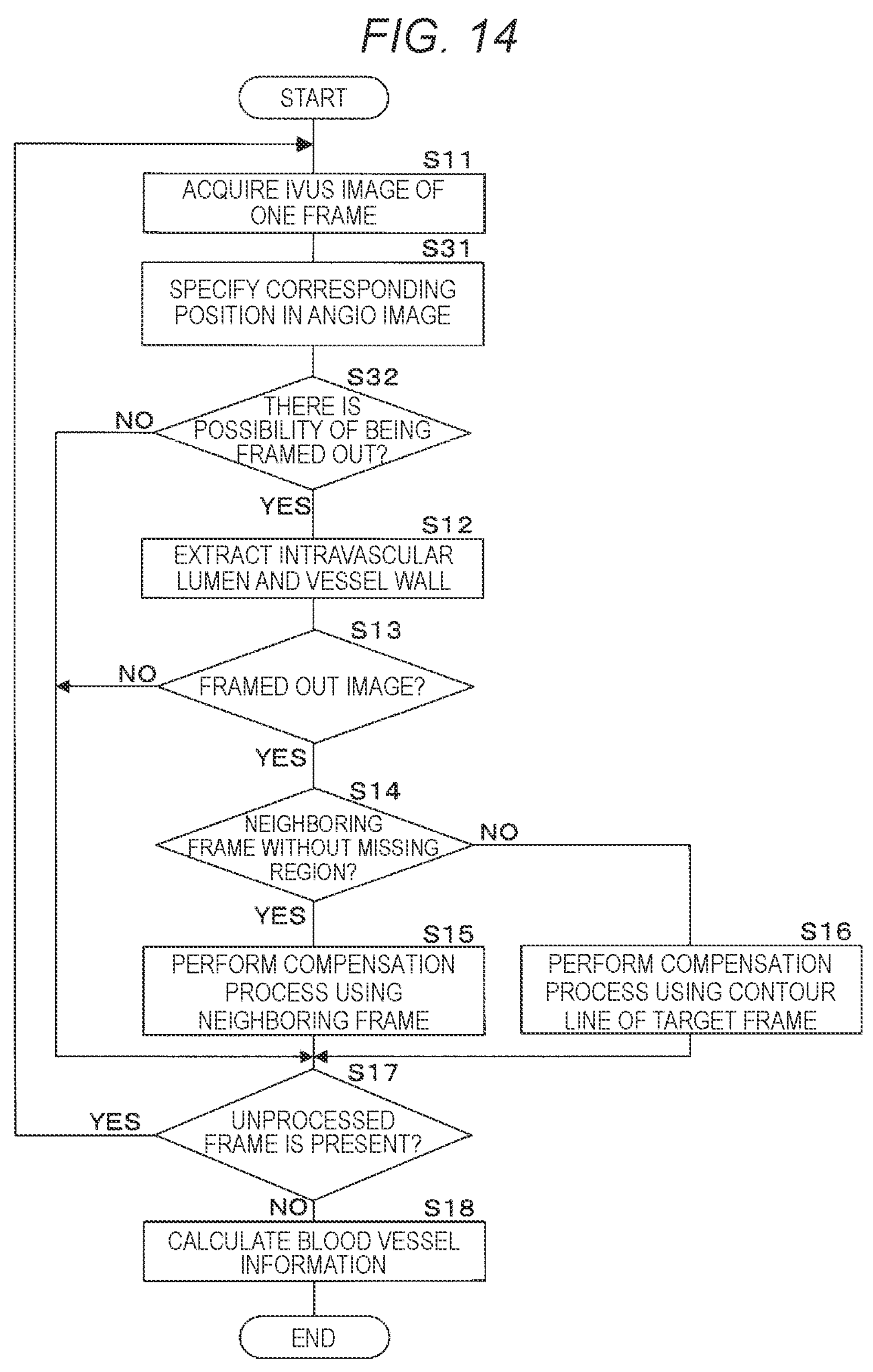
FIG. 14 is a flowchart showing an example of a compensation process procedure according to Embodiment 3.

FIG. 14 is a flowchart showing an example of a compensation process procedure according to Embodiment 3. In a process shown in FIGS. 14, S31 to S32 are added between S11 and S12 in the process shown in FIG. 5. Description of the same steps or processes as those in FIG. 5 is omitted. In the image processing device 3 according to the present embodiment, the control unit 31 performs the process of S11 shown in FIG. 5 to acquire the IVUS images to be processed.

The control unit 31 specifies the position in the angiogram corresponding to the imaging position of the acquired IVUS image (S31). For example, image information (for example, image numbers) of the IVUS image is given to each position in the angiogram, and the control unit 31 specifies the position to which the information of the IVUS image to be processed is given. Then, the control unit 31 determines, based on the specified position, whether there is a possibility that the intravascular lumen or the vessel wall in the IVUS image is framed out (S32). Here, for example, a region is set in advance, in which it is to be determined that there is the possibility that the intravascular lumen or the vessel wall in the IVUS image is framed out, and the control unit 31 may determine whether the specified position is included in the set region in the angiogram and determine whether the intravascular lumen or the vessel wall is framed out according to whether the specified position is included.

When the control unit 31 determines that there is a possibility that the IVUS image to be processed is framed out (S32: YES), the process proceeds to S12, and when the control unit 31 determines that there is no possibility that the IVUS image to be processed is framed out (S32: NO), the process proceeds to S17. Accordingly, when there is a possibility that the IVUS image to be processed is framed out, the control unit 31 executes the process of S12 and thereafter, determines whether the intravascular lumen or the vessel wall in the IVUS image to be processed is framed out, and performs the process of compensating the missing region when the intravascular lumen or the vessel wall is framed out. When there is no possibility that the intravascular lumen or the vessel wall is framed out, execution of an unnecessary process can be reduced and a processing speed can be increased by not performing the process of determining whether the intravascular lumen or the vessel wall is framed out.

In the present embodiment, the same effect as in the above embodiments can be obtained. In the present embodiment, it is determined whether the imaging position of the IVUS image is a place in which there is a possibility that the intravascular lumen or the vessel wall is framed out based on the angiogram, and thus an IVUS image which is captured at the position in which there is no possibility that the intravascular lumen or the vessel wall is framed out can be extracted. Accordingly, the process can be simplified by not performing the determination process as to whether the IVUS image which is captured at the position in which there is no possibility that the intravascular lumen or the vessel wall is framed out is framed out.

In the present embodiment, instead of the process of determining whether the imaging position of the IVUS image is the place having a possibility of being framed out based on the angiogram, it may be determined whether the imaging position is the place having the possibility of being framed out based on the IVUS image itself. Specifically, it may be determined whether the imaging position of the IVUS image is the place having the possibility of being framed out by using a blood vessel diameter obtained from the IVUS image. For example, when an imaging depth in the IVUS image is 6 mm and the blood vessel diameter at the imaging position of the IVUS image is 6 mm or more, the catheter 1*a* is biased to a vicinity of the vessel wall at the imaging position, and thus the possibility that the intravascular lumen or the vessel wall is framed out increases. Accordingly, it is possible to determine whether the imaging position is the place in which there is the possibility of being framed out based on the blood vessel diameter obtained from the IVUS image.

Also in the present embodiment, modifications appropriately described in the above embodiments can be applied. For example, instead of the IVUS image, when the intravascular lumen or the vessel wall is framed out, the process of compensating the missing region can be performed by the same process for an OCT image.

The detailed description above describes embodiments of a program, an image processing method, and an image processing device. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A non-transitory computer-readable medium storing a program executed by a computer that executes a process comprising:

acquiring a plurality of tomographic images of a cross section of a lumen organ captured at a plurality of places using a catheter, each tomographic image having an imaging range with a center corresponding to a position of the catheter;

extracting, from the plurality of tomographic images, a tomographic image in which a part of the lumen organ extends beyond the imaging range and is missing from the tomographic image; and compensating a missing region of the lumen organ that extends beyond the imaging range for the extracted tomographic image.

2. The computer-readable medium according to claim 1, further comprising:

inputting the plurality of acquired tomographic images into a learning model trained to output information indicating regions of a lumen and a lumen wall of a lumen organ in a tomographic image when the tomographic image is input, and outputting a lumen and a lumen wall of a lumen organ in each of the tomographic images; and extracting the tomographic image in which the part of the lumen organ is missing when a part of a contour line of the output lumen or lumen wall of the lumen organ matches a contour line of the tomographic image.

3. The computer-readable medium according to claim 1, further comprising:

in the extracted tomographic image in which the part of the lumen organ extends beyond the imaging range and is missing, compensating a contour line of the missing region of the lumen organ based on a contour line of the lumen organ which is not missing.

4. The computer-readable medium according to claim 1, further comprising:

compensating the missing region of the lumen organ in the extracted tomographic image based on a tomographic image in which the lumen organ is not missing in tomographic images captured in a vicinity of the extracted tomographic image.

5. The computer-readable medium according to claim 1, further comprising:

inputting the extracted tomographic image into a second learning model trained to output the missing region of the lumen organ in the extracted tomographic image when the extracted tomographic image in which the part of the lumen organ extends beyond the imaging range and is missing is input, and outputting the missing region of the lumen organ in the extracted tomographic image; and wherein compensating the missing region of the lumen organ in the extracted tomographic image is based on the output missing region of the lumen organ.

6. The computer-readable medium according to claim 1, further comprising:

adding, to the extracted tomographic image in which the part of the lumen organ extends beyond the imaging range and is missing, a contour line of the compensated missing region of the lumen organ in a mode of indicating a compensated place.

7. The computer-readable medium according to claim 2, wherein the lumen organ is a blood vessel, the lumen is an intravascular lumen, and the lumen wall is a vessel wall.

8. An image processing method of executing processes by a computer, the image processing method comprising:

acquiring a plurality of tomographic images of a cross section of a lumen organ captured at a plurality of places using a catheter, each tomographic image having an imaging range with a center corresponding to a position of the catheter;

extracting, from the plurality of tomographic images, a tomographic image in which a part of the lumen organ extends beyond the imaging range and is missing from the tomographic image; and compensating a missing region of the lumen organ that extends beyond the imaging range for the extracted tomographic image.

9. The method according to claim 8, further comprising:

inputting the plurality of acquired tomographic images into a learning model trained to output information indicating regions of a lumen and a lumen wall of a lumen organ in a tomographic image when the tomographic image is input, and outputting a lumen and a lumen wall of a lumen organ in each of the tomographic images; and extracting the tomographic image in which the part of the lumen organ is missing when a part of a contour line of the output lumen or lumen wall of the lumen organ matches a contour line of the tomographic image.

10. The method according to claim 8, further comprising:

in the extracted tomographic image in which the part of the lumen organ extends beyond the imaging range and is missing, compensating a contour line of the missing region of the lumen organ based on a contour line of the lumen organ which is not missing.

11. The method according to claim 8, further comprising:

compensating the missing region of the lumen organ in the extracted tomographic image based on a tomographic image in which the lumen organ is not missing in tomographic images captured in a vicinity of the extracted tomographic image.

12. The method according to claim 8, further comprising:

inputting the extracted missing tomographic image into a second learning model trained to output the missing region of the lumen organ in the extracted tomographic image when the tomographic image in which the part of the lumen organ extends beyond the imaging range and is missing is input and outputting the missing region of the lumen organ in the extracted tomographic image; and wherein compensating the missing region of the lumen organ in the extracted tomographic image is based on the output missing region of the lumen organ.

13. The method according to claim 8, further comprising:

adding, to the extracted tomographic image in which the part of the lumen organ extends beyond the imaging range and is missing, a contour line of the compensated missing region of the lumen organ in a mode of indicating a compensated place.

14. The method according to claim 9, wherein the lumen organ is a blood vessel, the lumen is an intravascular lumen, and the lumen wall is a vessel wall.

15. An image processing device comprising:

a processor configured to:

acquire a plurality of tomographic images of a cross section of a lumen organ captured at a plurality of places using a catheter, each tomographic image having an imaging range with a center corresponding to a position of the catheter;

extract, from the plurality of tomographic images, a tomographic image in which a part of the lumen organ extends beyond the imaging range and is missing from the tomographic image; and compensate a missing region of the lumen organ that extends beyond the imaging range for the extracted tomographic image.

16. The image processing device according to claim 15, wherein the processor is further configured to:

input the plurality of acquired tomographic images into a learning model trained to output information indicating regions of a lumen and a lumen wall of a lumen organ in a tomographic image when the tomographic image is input, and outputting a lumen and a lumen wall of a lumen organ in each of the tomographic images; and extract the tomographic image in which the part of the lumen organ is missing when a part of a contour line of the output lumen or lumen wall of the lumen organ matches a contour line of the tomographic image.

17. The image processing device according to claim 15, wherein the processor is further configured to:

in the extracted tomographic image in which the part of the lumen organ extends beyond the imaging range and is missing, compensate a contour line of the missing region of the lumen organ based on a contour line of the lumen organ which is not missing.

18. The image processing device according to claim 15, wherein the processor is further configured to:

compensate the missing region of the lumen organ in the extracted tomographic image based on a tomographic image in which the lumen organ is not missing in tomographic images captured in a vicinity of the extracted tomographic image.

19. The image processing device according to claim 15, wherein the processor is further configured to:

input the extracted missing tomographic image into a second learning model trained to output the missing region of the lumen organ in the extracted tomographic image when the tomographic image in which the part of the lumen organ extends beyond the imaging range and is missing is input, and outputting the missing region of the lumen organ in the extracted tomographic image; and wherein compensate the missing region of the lumen organ in the extracted tomographic image is based on the output missing region of the lumen organ.

20. The image processing device according to claim 15, wherein the processor is further configured to:

add, to the extracted tomographic image in which the part of the lumen organ extends beyond the imaging range and is missing, a contour line of the compensated missing region of the lumen organ in a mode of indicating a compensated place.

* * * * *